(12) United States Patent
Dong et al.

(10) Patent No.: US 8,394,585 B2
(45) Date of Patent: Mar. 12, 2013

(54) DNA METHYLATION DETECTION METHODS

(75) Inventors: Shoulian Dong, Mountain View, CA (US); Junko Stevens, Menlo Park, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/180,382

(22) Filed: Jul. 11, 2011

(65) Prior Publication Data

US 2012/0149012 A1 Jun. 14, 2012

Related U.S. Application Data

(63) Continuation of application No. 12/543,450, filed on Aug. 18, 2009, now abandoned.

(60) Provisional application No. 61/089,856, filed on Aug. 18, 2008.

(51) Int. Cl.
*C12Q 1/68* (2006.01)

(52) U.S. Cl. ......................................... 435/6.1

(58) Field of Classification Search ................ None
See application file for complete search history.

(56) References Cited

U.S. PATENT DOCUMENTS

| | | |
|---|---|---|
| 2002/0197639 A1 | 12/2002 | Shia et al. |
| 2005/0196792 A1 | 9/2005 | Fodor et al. |
| 2006/0204988 A1 | 9/2006 | Fassbender et al. |
| 2006/0240460 A1 | 10/2006 | Pfeifer et al. |
| 2010/0041057 A1 | 2/2010 | Dong et al. |

FOREIGN PATENT DOCUMENTS

| | | |
|---|---|---|
| WO | WO-2007/081791 A2 | 7/2007 |
| WO | WO-2010/022098 | 2/2010 |
| WO | WO-2010/022098 A3 | 5/2010 |

OTHER PUBLICATIONS

U.S. APpl. No. 12/543,450 Office Action dated Feb. 11, 2011.
U.S. Appl. No. 12/543,450 Office Action dated Sep. 21, 2010.
PCT/US2009/054220 International Search Report dated Mar. 30, 2010.
PCT/US2009/054220 International Preliminary Report dated Mar. 3, 2010.
Mario, F., et al. "The affinity of different MBD proteins for a specific methylated locus depends on their intrinsic binding properties" Nucleic Acids Research, vol. 31, No. 6 (2003) pp. 1765-1774.

*Primary Examiner* — Christopher M. Babic

(57) ABSTRACT

The present teachings provide DNA methylation quantification methods that avoid bisulfite treatment of DNA. Methylation-specific binding proteins (MeDNA binding proteins) and non-methylation specific binding proteins (non-MeDNA binding proteins) are employed in various embodiments to modulate the accessibility of nucleic acids to primer extension reactions. After selectively removing the target nucleic acids, the extension products can be analyzed and methylation quantitated. In some embodiments, the analysis comprises real-time PCR.

38 Claims, 14 Drawing Sheets

Block further extension of the first primer

Block initial extension of the first primer

Block primer hybridization

Block further extension of the first primer

Block initial extension of the first primer

Block primer hybridization

Names and Designs of Oligonucleotides

- Synthetic template:

A. With central Me-dC:
  CCCCGCGAGCACAGATAAATGGCTTAG(Me-C)GTAGTTTAGTAGGGATCGTGCCGGGCGCCAGGAA B. With additional 1-4 dU (used to test antibody protection):
  CCCCGCGAGCACAGATAAAUGGCTTAG(Me-C)GUAGTTUAGTAGGGAUCGTGCCGGGCGCCAGGAA C. With Me-dC at priming site (FAM labeled Probe):
  CCCCGCGAGCACAGATAAAUGGCTTAG(Me-C)GUAGTTUAGTAGGGAUCGTGC(Me-C)GG(Me-C)GCCAGGAA D. Alternative template for MeDNA differentiation duplex assays (VIC Labeled Probe):
  CCCCGCGAGCACAGATAAAUAGGGTTTA(Me-dC)GUGATUAGTGGGAUCGTGCCGAUCGTGCCGGGCGCCAGGAA

- Primers:
  - Forward (Pr-F): CCCCGCGGAGCACAGA
  - Reverse w/o modification (Pr-R): TTCCTGCCGCCGGC
  - Reverse with Me-dC(Pr-R-Me): TTCCTGG(Me-C)GC(Me-C)GGC

- Probes:
  - FAM: (6-FAM)TGGCTTAGCGTAGTTTAGTAGG(MGB)
  - VIC: (VIC)TAGGGTTTACGTGATTAGTGGC(MGB)

*FIG. 7A*

Differentiation of Template Methylation Status by M.SssI: Protocols

(1) M.SssI Binding

Add M.SssI (NEB) to 1.6 U/ul reaction with 4 pM each methylated (C) and non-methylated (D) DNA templates, 80 nM reverse primer (Pr-R), 100 mM Tris-HCl, pH 8.3, 6 mM $MgCl_2$, 600 uM each of dATP, dCTP, dGTP and dTTP, 320 uM S-(5'-adenosyl)-homocysteine (SAC), and 150 mM KCl.

Mix well and spin down. Incubate at 37°C for 60 min on a ABI 7900 PCR thermal cycler.

(2) Complementary strand synthesis

Add 5 ul 2.5 U/ul ArrayScript reverse transcriptase (Ambion) to M.SssI bound DNA mix in (1).

Mix well and spin down. On a ABI 7900 PCR thermal cycler, incubate at 37°C for 15 min and heat inactivate enzymes at 95°C for 10 min.

(3) Template removal and PCR

Use 4 ul 1:10 diluted synthesized DNA in (2) in 20 ul PCR reaction with 900 nM forward (Pr-F) and reverse (Pr-R) primers and 200 nM each of FAM and VIC labeled probes in 1x GeneExpression Master Mix (Applied Biosystems).

Incubate at 50°C for 15 min before standard PCR cycling (95°C/10 min followed by 40 cycles of 95°C/15 sec and 60°C/1min) on 7900 HTS.

Compare FAM and VIC Ct differences to reactions with added 0.04 U/ul UDG.

*FIG. 7D*

Single template; no added salt to the reaction
Antibody binding dose-dependently hindered reverse transcription, more for MeDNA
Binding constant of antibody between 0.04 - 0.2 ug/20 ul (13 nM - 66 nM)
Low differentiation (~ 10 fold) of methylated and non-methylated template

DNA METHYLATION DETECTION METHODS

CROSS-REFERENCE TO RELATED APPLICATIONS

This application is a Continuation of U.S. patent application Ser. No. 12/543,450 filed Aug. 18, 2009, now abandoned, which claims priority to U.S. Provisional Patent Application Ser. No. 61/089,856 filed Aug. 18, 2008 which disclosures are herein incorporated by reference in their entirety.

FIELD

The present teachings pertain to methods and kits for quantitating cytosine methylation in target nucleic acids.

INTRODUCTION

Epigenomic changes to DNA provide another channel of information on which natural selection can act (see Goldberg et al., Cell, 128: 635-638). Increasing attention is being paid to methylation of bases in nucleic acids as one important epigenomic change. Methylation of bases can take different forms. For example, methylation of DNA by the DNA adenine methyltransferase (Dam) provides an epigenetic signal that influences and regulates numerous physiological processes in the bacterial cell including chromosome replication, mismatch repair, transposition, and transcription (see Heusipp et al., Int J Med Microbiol. 2007 February; 297(1):1-7. Epub 2006 Nov. 27 for a review). Also, methylation of cytosine in mammals at CpG dinucleotides correlates with transcriptional repression, and plays a crucial role in gene regulation and chromatin organization during embryogenesis and gametogenesis (Goll and Bestor (2006) Annu. Rev. Biochem. 74, 481-514).

One method of measuring the presence of cytosine methylation takes advantage of the ability of the converting agent bisulfite to convert non-methylated cytosines to uracil (See Boyd et al., Anal Biochem. 2004 Mar. 15; 326(2):278-80, Anal Biochem. 2006 Jul. 15; 354(2):266-73. Epub 2006 May 6, and Nucleosides Nucleotides Nucleic Acids. 2007; 26(6-7):629-34. After such conversion, a sequence amplified in a PCR bears thymine at those residues that were originally unmethylated cytosine. However, methylated cytosines are protected from such bisulfite treatment. Accordingly, the presence of a thymine at a location known to normally contain cytosine reflects that the original cytosine was unmethylated. Conversely, the presence of a cytosine at a location known to normally contain cytosine reflects that the original cytosine was methylated.

Following bisulfite conversion, and PCR amplification, sequences containing a large number of unmethylated cytosines will have a low complexity, since the non-methylated cytosines will have been converted to thymine, and the resulting sequence will be dominated by only three bases (A, G, and T). Such low complexity sequences can be difficult to map to a region (locus) of the genome. That is, when a low complexity nucleic acid is sequenced, it can be difficult to know what part of the genome the sequence comes from. Such a problem is particularly acute in various sequencing approaches that employ short read-lengths.

Bisulfite treatment is also problematic because of limited sample size. Treatment is harsh, and small amounts of starting material are not easily analyzed using bisulfite.

SUMMARY

A method of quantitating methylation in a target nucleic acid comprising;

treating a target nucleic acid with a MeDNA binding protein, wherein the MeDNA binding protein forms a blocking complex with a methylated cytosine in the target nucleic acid, wherein the methylated cytosine in the target nucleic acid is near a first target specific primer binding site;

extending a first target specific primer hybridized to the first target specific primer binding site to form a target nucleic acid extension product;

degrading the target nucleic acid;

amplifying the target nucleic acid extension product;

determining the difference between the amount of the target nucleic acid with the amount of a control nucleic acid lacking a methylated cytosine; and, quantitating methylation in the target nucleic acid.

BRIEF DESCRIPTION OF THE DRAWINGS

FIG. 7A shows exemplary oligonucleotides in accordance with embodiments of the present invention;

FIG. 7D shows exemplary protocols in accordance with an embodiment of the present invention;

DESCRIPTION OF EXEMPLARY EMBODIMENTS

Figure 1:
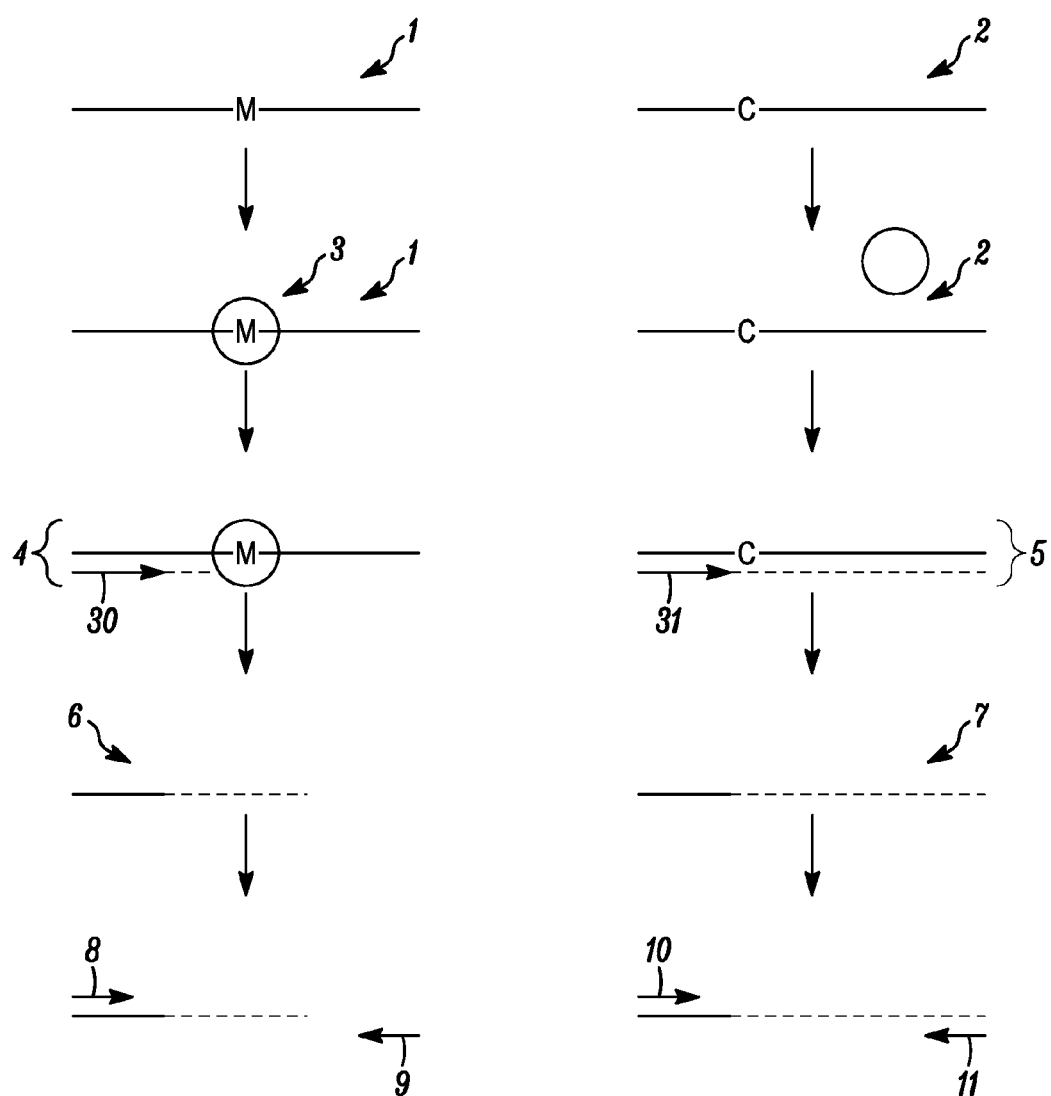
FIG. 1 shows a schematic illustration of an exemplary method of an embodiment of the present invention.

It is to be understood that both the foregoing general description and the following detailed description are exemplary and explanatory only and are not intended to limit the scope of the current teachings. In this application, the use of the singular includes the plural unless specifically stated otherwise. Also, the use of "comprise", "contain", and "include", or modifications of those root words, for example but not limited to, "comprises", "contained", and "including", are not intended to be limiting. The use of "or" means "and/or" unless stated otherwise. The term and/or means that the terms before and after can be taken together or separately. For illustration purposes, but not as a limitation, "X and/or Y" can mean "X" or "Y" or "X and Y".

The section headings used herein are for organizational purposes only and are not to be construed as limiting the described subject matter in any way. All literature and similar materials cited in this application, including, patents, patent applications, articles, books, treatises, and internet web pages are expressly incorporated by reference in their entirety for any purpose. In the event that one or more of the incorporated literature and similar defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

SOME DEFINITIONS

As used herein, the term "degrading" refers to removal of unwanted nucleic acids in a reaction. Such degradation can be achieved, for example, by employing first primers in the primer extension reaction that contain a nuclease resistant blocking moiety, thus protecting extension products from nuclease degradation. Examples of suitable blocking moieties and nuclease-mediated approaches are known in the art, and are described for example in Chen et al., U.S. Pat. No. 7,208,278, Greenfield et al., U.S. patent application Ser. No. 10/202,211, and Barany et al., U.S. Pat. No. 6,797,470.

As used herein, the term "amplifying" refers to any process that increases the amount of a desired nucleic acid. Any of a variety of known amplification procedures can be employed in the present teachings, including PCR (see for example U.S. Pat. No. 4,683,202), as well as any of a variety of ligation-mediated approaches, including LDR and LCR (see for example U.S. Pat. No. 5,494,810, U.S. Pat. No. 5,830,711, U.S. Pat. No. 6,054,564). Some other amplification procedures include isothermal approaches such as rolling circle amplification and helicase-dependant amplification.

As used herein, the term "blocking complex" refers to a structure formed by the interaction of a methylated cytosine with a MeDNA binding protein, as well as the structure formed by the interaction of an unmethylated cytosine with a non-MeDNA binding protein. Both situations bring about the inability of a primer extension reaction to proceed given the presence of the blocking complex.

As used herein, the term "cytosine position of interest" refers to a cytosine residue in a nucleic acid whose methylation status is relevant to the experimentalist.

As used herein, the term "near a primer binding site" and various usages of it, refers to the location of a cytosine of interest in a nucleic acid, in reference to the position of a first primer. Thus, a cytosine of interest can be in the sequence of the primer binding site, or can be 1, 2 or fewer, 3 or fewer, 4 or fewer, 5 or fewer, 6 or fewer, 7 or fewer, 8 or fewer, 9 or fewer, 10 or fewer, 11 or fewer, 12 or fewer, 13 or fewer, 14 or fewer, 15 or fewer, 16 or fewer, 17 or fewer, 18 or fewer, 19 or fewer, 20 or fewer, 21 or fewer, 22 or fewer, 23 or fewer, 24 or fewer, 25 or fewer, 26 or fewer, 27 or fewer, 28 or fewer, 29 or fewer, 30 or fewer, 30-40, 40-50, 50-60, 60-70, 70-100, 100-150, 150-300, 300-500, or 500-1000, nucleotides away from the 3' end of the first primer. The various embodiments depicted in FIGS. 3 and 6 illustrate situations where the cytosine position of interest is near a primer binding site.

As used herein, the term "cofactor" refers to compounds that binds to an enzyme to facilitate enzyme catalysis. In those embodiments employing a MeDNA binding protein, cofactors serve the function of modulate the binding of the protein to DNA. In those embodiments employing a non-MeDNA binding protein, cofactors serve the function of providing transferable chemical motif for the enzyme reaction.

As used herein, the term "first primer" refers generally to the primer employed in the extension reaction. A first control specific primer is one example of a first primer. A first control specific primer hybridizes to a "first control specific primer site." A first target specific primer is another example of a first primer. A first target specific primer hybridizes to a "first target specific primer site".

As used herein, the term "second primer" refers generally to a primer employed in a PCR, which hybridizes to the extension product produced in the extension reaction, and which can extend to form a complementary strand. In those embodiments in which the amplifying is a PCR, a first primer can hybridize to the complementary strand generated by extension of the second primer, and itself become extended to effectuate the PCR process. A second control specific primer is one example of a second primer. A second control specific primer can hybridize to a "control specific extension product". A second target specific primer is another example of a second primer. A second target specific primer hybridizes to a "target specific extension product".

As used herein, the term "extension product" refers generally to the result of a primer extension reaction. A target specific extension product is one example of an extension product, it resulting from extension of a first target specific primer. A control specific extension product is another example of an extension product, it resulting from extension of a first control specific primer.

As used herein, the term "MeDNA binding protein" refers to a protein that binds methylated cytosine in a nucleic acid, thus forming a binding complex. Examples of MeDNA binding proteins include MeCP2, MBD1, MBD2, MBD3 and MBD4 (Fraga, MF, et al Nucleic Acid Research, 2003, 31(6), 1765-1774), Dnmt1 (Cheng, X. and Blumenthal RM Structure, 2008, 16, 341-350), methyl-CpG antibodies, recombinant proteins with multiple methyl-DNA-binding domains (Jorgensen, H F. Et al Nucleic Acid Research, 2006, 34(13), e96), McrBC, and VIM1 (Woo, H R et al Genes & Development, 2007, 21, 267-277).

As used herein, the term "non MeDNA binding protein" refers to a protein that binds unmethylated cytosine in a nucleic acid, thus forming a binding complex. Examples of non-MeDNA biding proteins include Dnmt3a and Dnmt3b ((Cheng, X. and Blumenthal RM Structure, 2008, 16, 341-350), M. Sssl (Flynn, J. et al Biochemistry, 1996, 35, 7308-7315), CXXC domain of MDB1 (Voo, K S et al Mol. Cell Biol. 2000, 20, 2108-2021).

As used herein, the term "Ct value" refers to a cycle in a PCR at which a particular intensity of a probe is observed. Examples of PCR analysis using Ct values can be found in U.S. Pat. No. 7,132,239, U.S. Pat. No. 7,057,025, U.S. Pat. No. 6,890,718, U.S. Pat. No. 5,952,202, U.S. Pat. No. 6,884,583, and U.S. Pat. No. 6,432,642.

MeDNA Binding Protein Embodiments

In some embodiments, the present teachings provide a method of quantitating methylation in a target nucleic acid. For example, in some embodiments, the present teachings provide a method of quantitating methylation in a target nucleic acid comprising; treating a target nucleic acid with a MeDNA binding protein, wherein the MeDNA binding protein forms a blocking complex with a methylated cytosine in the target nucleic acid, wherein the methylated cytosine in the target nucleic acid is near a first target specific primer binding site; extending a first target specific primer hybridized to the first target specific primer binding site to form a target nucleic acid extension product; degrading the target nucleic acid; amplifying the target nucleic acid extension product; determining the difference between the amount of the target nucleic acid with the amount of a control nucleic acid lacking a methylated cytosine; and, quantitating methylation in the target nucleic acid.

In some embodiments, the amplifying comprises a polymerase chain reaction comprising a first target specific primer and a second target specific primer.

In some embodiments, the degrading comprises treating the target nucleic acid with a nuclease, wherein the target nucleic acid extension product is resistant to the nuclease due to a blocking moiety in the first target specific primer.

One illustrative embodiment is depicted in FIG. 1. Here, a target nucleic acid (1) containing a methylated cytosine residue (M) is present in a reaction mixture. A control nucleic acid (2) contains an unmethylated cytosine (C). The target nucleic acid can be treated with a MeDNA binding protein (oval shape), which can form a blocking complex with a methylated cytosine in the target nucleic acid (3). The control nucleic acid, lacking a methylated cytosine, fails to form a blocking complex with the MeDNA binding protein (note that the oval, representing the MeDNA binding protein, is not bound with the unmethylated cytosine (C) in the control nucleic acid (2). A primer extension reaction can be attempted by hybridizing a first target specific primer (30) to the target nucleic acid, and a first control specific primer (31) to the control nucleic acid. The target nucleic acid with the methylated cytosine, due to the blocking complex with the MeDNA binding protein, is unable to undergo primer extension (4), producing for example truncated extension products (6). However, the control nucleic acid with the unmethylated cytosine is able to undergo primer extension (5) due to the absence of a blocking complex, thus forming a control nucleic acid extension product (dashed, (7)). The target nucleic acid and control nucleic can then be degraded (note the absence of (1) and (2)), leaving extension products in tact. Amplifying the extension products can then be performed, here shown by a PCR using a first target specific primer (8) and a second target specific primer (9) for the target nucleic acid, and a first control specific primer (10) and a second control specific primer (11) for the control nucleic acid. Determining the difference between the amount of the target nucleic acid with the amount of a control nucleic acid lacking a methylated cytosine allows for quantitating methylation in the target nucleic acid. Here, amplification can proceed on the control extension product, but fails on the truncated target extension product.

Figure 2A:
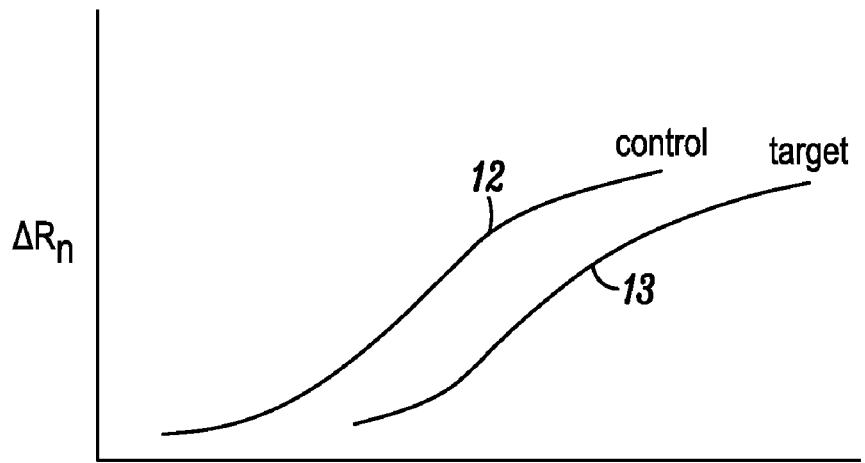
FIGS. 2A and 2B show illustrative graphs arising from an exemplary method of an embodiment of the present invention.

Illustrative graphs arising from practice of the method of FIG. 1, are depicted in FIG. 2. FIG. 2A shows the hypothetical results of an experiment in which the target nucleic acid is more methylated than the control nucleic acid. Here, the results of a real-time PCR illustrate that the Ct value for the control nucleic acid (12) is lower (left-shifted) than the Ct value for the target nucleic acid (13). This shift reflects the greater number of extension products resulting from the extension reaction of the control nucleic acid as compared to the target nucleic acid. This can be interpreted to reflect that the MeDNA binding protein preferentially bound target nucleic acids containing methylated cytosine to form blocking complexes, thus preventing the formation of target nucleic acid extension products. Thus, the target nucleic acids contain a greater amount of methylated cytosine at the cytosine position of interest than do the control nucleic acids.

Figure 2B:
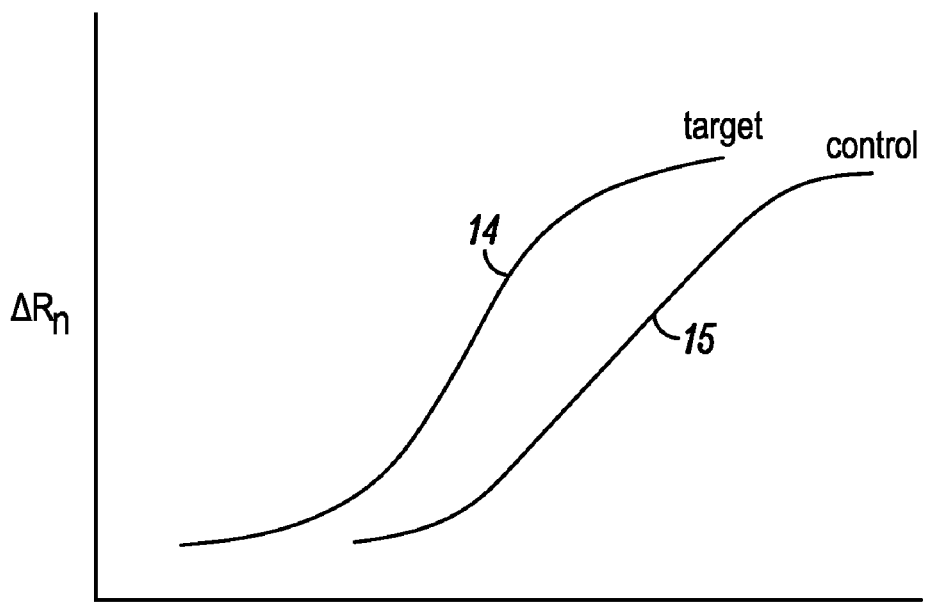

FIG. 2B shows the hypothetical results of an experiment in which the target nucleic acid is less methylated than the control nucleic acid. Here, the results of a real-time PCR illustrate that the Ct value for the target nucleic acid (14) is lower (left-shifted) than the Ct value for the control nucleic acid (15). This shift reflects the greater number of extension products resulting from the extension reaction of the target nucleic acid as compared to the control nucleic acid. This can be interpreted to reflect that the MeDNA binding protein preferentially bound control nucleic acids containing methylated cytosine to form blocking complexes, thus preventing the formation of control nucleic acid extension products. Thus, the target nucleic acids contain a lesser amount of methylated cytosine at the cytosine position of interest than do the control nucleic acids.

Figure 3A:
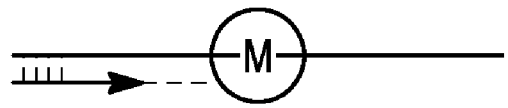
FIGS. 3A, 3B and 3C show schematic aspects of exemplary blocking complexes in accordance with embodiments of the present invention.
Figure 3B:
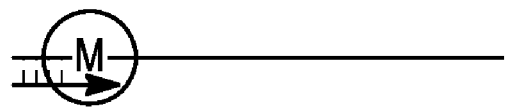
Figure 3C:
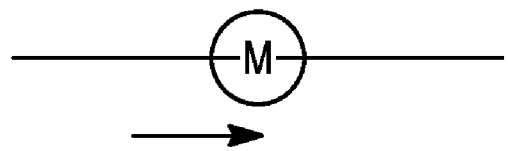

FIG. 3 illustrates some various possible relationships between the location of a cytosine of interest, the blocking complex formed with the MeDNA binding protein, and the first primer. In some embodiments, the first primer hybridizes upstream from the blocking complex formed by the MeDNA binding protein and the methylated cytosine in the target nucleic acid, and further extension of the first primer is blocked. This is depicted in FIG. 3A. Note that in FIG. 3A the first primer is shown hybridized (see vertical lines indicating Hydrogen bonds) upstream from the cytosine of interest, and that the primer is partially extended (dashed horizontal line). However, the blocking complex between the methylated cytosine and the MeDNA binding protein blocks further extension of the first primer. In some embodiments, the first primer hybridizes on the methylated cytosine on the blocking complex formed by the MeDNA binding protein and the methylated cytosine in the target nucleic acid, and initial extension of the first primer is blocked. This is depicted in FIG. 3B. Note than in FIG. 3B the first primer is shown hybridized (see the vertical lines indicating Hydrogen bonds) on the cytosine of interest, and that the primer is not extended. The blocking complex between the methylated cytosine and the MeDNA binding protein blocks initial extension of the first primer. In some embodiments, the first primer does not hybridize to the methylated cytosine on the blocking complex formed by the MeDNA binding protein and the methylated cytosine in the target nucleic acid. This is depicted in FIG. 3C. Note the absence of vertical lines between the first primer and the target nucleic acid, indicating that the blocking complex formed by the MeDNA binding protein and the methylated cytosine in the target nucleic acid prevents the first primer from hybridizing. As will be appreciated by one of ordinary skill in the art in light of the present teachings, the choice of position between the cytosine of interest, the MeDNA binding protein, and the primer binding site can be chosen according to the experimentalist using routine experimentation.

The control nucleic acid can be employed in a variety of ways. For example, the control nucleic acid can be in the same reaction mixture as the target nucleic acid and can be a different sequence than the target nucleic acid. The control nucleic acid can be of a known concentration, and can be known to contain an unmethylated cytosine or a particular amount of unmethylated cytosine at the position of interest. In some embodiments, the control nucleic acid can be in a different reaction mixture from the target nucleic acid. For example, the control nucleic acid can be the same sequence as the target nucleic acid, and can be present in a known amount in the different reaction mixture. In some embodiments, the control nucleic acid can be a different sequence than the target nucleic acid, and can be present in a known amount in the different reaction mixture. Various methods of performing the control reactions will be appreciated by one of skill in the art in light of the present teachings, including for example employing controls of the appropriate abundance class (see Bodeau et al., U.S. patent application Ser. No. 11/372,242.

The present teachings also provide a method of quantitating methylation in a target nucleic acid comprising;
treating, in any order,
(a) the target nucleic acid with a MeDNA binding protein, wherein the MeDNA binding protein forms a blocking complex with a methylated cytosine in the target nucleic acid, wherein the methylated cytosine is disposed between a first target specific primer binding site and a second target specific primer binding site; and,
(b) a control nucleic acid with a MeDNA binding protein, wherein the MeDNA binding protein fails to form a blocking complex with an unmethylated cytosine in the control nucleic acid, wherein the non-methylated cytosine is disposed between a first control specific primer binding site and a second control specific primer binding site;
extending, in any order,
(a) a first target specific primer hybridized to the first target specific primer binding site to form a target nucleic acid extension product; and,
(b) a first control specific primer hybridized to the first control specific primer binding site to form a control nucleic acid extension product;
degrading, in any order,
(a) the target nucleic acid; and,
(b) the control nucleic acid;
amplifying, in any order,
(a) the target nucleic acid extension product in a polymerase chain reaction comprising a first target specific primer and a second target specific primer; and,
(b) the control nucleic acid extension product in a polymerase chain reaction comprising a first control specific primer and a second control specific primer;
determining the difference between the amount of target nucleic acid with the amount of control nucleic acid; and,
quantitating methylation in the target nucleic acid.
In some embodiments, the determining comprises;
measuring, in any order,
(a) a first Ct value associated with the amount of the target nucleic acid, and,
(b) a second Ct value associated with the amount of the control nucleic acid; and,
quantitating methylation in the target nucleic by comparing the first Ct value with the second Ct value.
In some embodiments, the first Ct value is higher than the second Ct value, and the target nucleic acid is more methylated than the control nucleic acid.
In some embodiments, the first Ct value is lower than the second Ct value, and the target nucleic acid is less methylated than the control nucleic acid.
In some embodiments, the target nucleic acid and the control nucleic acid comprise the same first primer binding site and the same second primer binding site.
In some embodiments, the target nucleic acid is amplified in a separate reaction vessel from the control nucleic acid.
In some embodiments, the target nucleic acid and the control nucleic acid comprise the same first primer binding site and the same second primer binding site and are amplified with a common first primer and a common second primer.
In some embodiments, the target nucleic acid is amplified in a same reaction vessel as the control nucleic acid.

In some embodiments, the target nucleic acid and the control nucleic acid comprise a different first primer binding site and a different second primer binding site and are amplified with a different first primer and a different second primer.

In some embodiments, the quantitating comprises measuring an interchelating dye.

In some embodiments, the determining comprises;
measuring displacement of a target sequence specific probe, wherein the target sequence specific probe hybridizes to a region of the target nucleic acid extension product, or complement to the target nucleic acid extension product, disposed between the first target specific primer binding site and the second target specific primer binding site;
measuring displacement of a control sequence specific probe, wherein the control sequence specific probe hybridizes to a region of the control nucleic acid extension product, or complement to the control nucleic acid extension product, disposed between the first control specific primer binding site and the second control specific primer binding site.

In some embodiments, the treating with the MeDNA binding protein further comprises a cofactor.

In some embodiments, the cofactor is selected from the group consisting of S-adenosylmethionine, S-adenosylhomocysteine and sinefungin. In a preferred embodiment, S-adenosylhomocycteine is used.

In some embodiments, the first primer hybridizes upstream from the blocking complex formed by the MeDNA binding protein and the methylated cytosine in the target nucleic acid, and further extension of the first primer is blocked.

In some embodiments, the first primer hybridizes on the methylated cytosine on the blocking complex formed by the MeDNA binding protein and the methylated cytosine in the target nucleic acid, and initial extension of the first primer is blocked.

In some embodiments, the first primer does not hybridize to the methylated cytosine on the blocking complex formed by the MeDNA binding protein and the methylated cytosine in the target nucleic acid.

Non-MeDNA Binding Protein Embodiments

In some embodiments, the present teachings provide a method of quantitating methylation in a target nucleic acid. For example, in some embodiments, the present teachings provide a method of quantitating methylation in a target nucleic acid comprising; treating a control nucleic acid with a non-MeDNA binding protein, wherein the non-MeDNA binding protein forms a blocking complex with an unmethylated cytosine in the control nucleic acid, wherein the unmethylated cytosine in the control nucleic acid is near a first control specific primer binding site; extending a first primer hybridized to the first primer binding site to form a control nucleic acid extension product; degrading the control nucleic acid; amplifying the control nucleic acid extension product; determining the difference between the amount of the control nucleic acid with the amount of a target nucleic acid containing a methylated cytosine; and, quantitating methylation in the target nucleic acid.

In some embodiments, the amplifying comprises a polymerase chain reaction comprising a first target specific primer and a second target specific primer.

In some embodiments, the degrading comprises treating the target nucleic acid with a nuclease, wherein the target nucleic acid extension product is resistant to the nuclease due to a blocking moiety in the first target specific primer.

Figure 4:
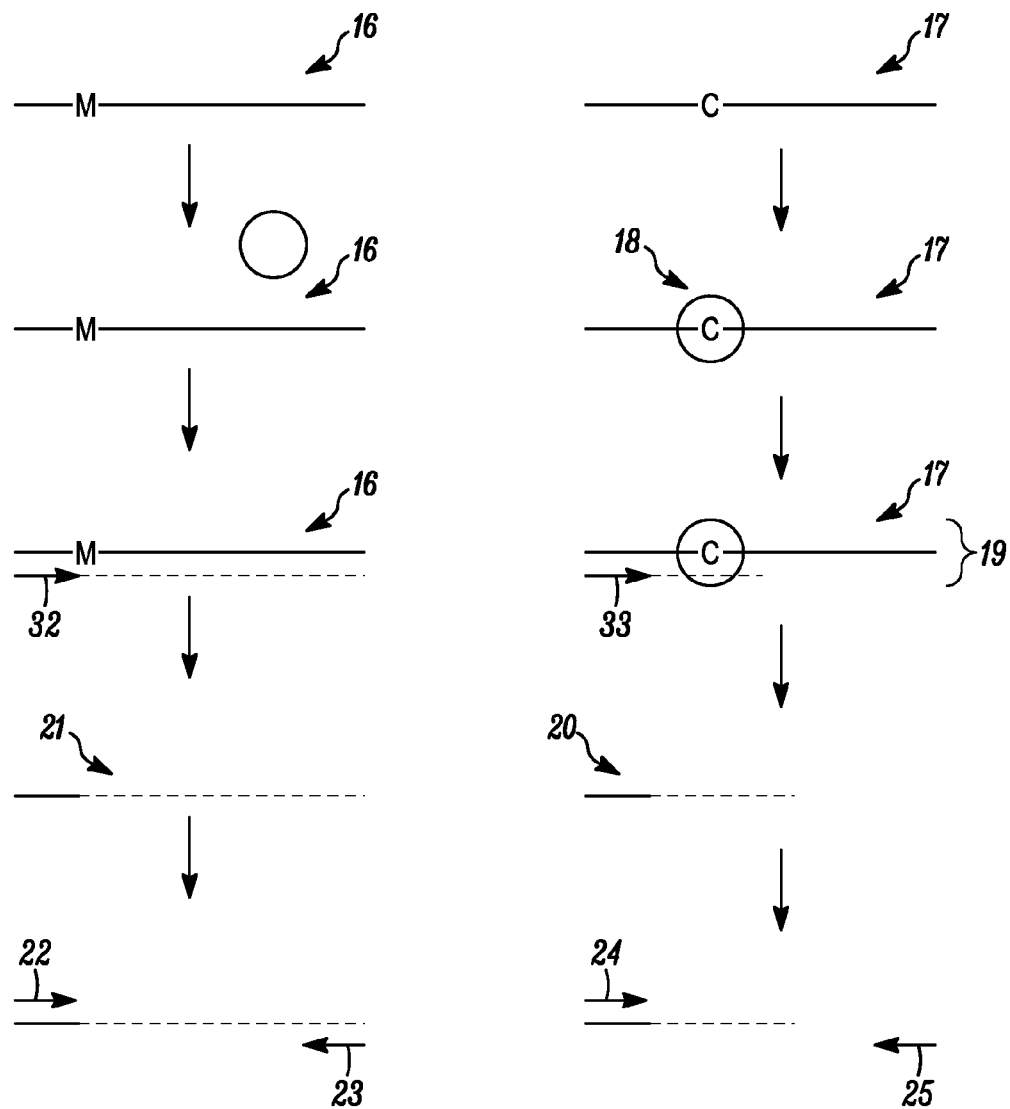
FIG. 4 shows a schematic illustration of an exemplary method of an embodiment of the present invention.

One illustrative embodiment is depicted in FIG. 4. Here, a target nucleic acid (16) containing a methylated cytosine residue (M) is present in a reaction mixture. A control nucleic acid (17) contains an unmethylated cytosine (C). The target nucleic acid can be treated with a non-MeDNA binding protein (oval shape), but due to the presence of a methyl group on the cytosine of interest, fails to form a blocking complex with the non-MeDNA binding protein (note that the oval shape, representing the non-MeDNA binding protein, is not bound with the methylated cytosine (C) in the target nucleic acid (16)). The control nucleic acid, lacking a methylated cytosine, is able to form a blocking complex (18) with the non-MeDNA binding protein (note that the oval, representing the MeDNA binding protein, is bound with the unmethylated cytosine (C) in the control nucleic acid (17). A primer extension reaction can be performed. The control nucleic acid with the unmethylated cytosine, due to the blocking complex with the non-MeDNA binding protein, is unable to undergo primer extension (19) with a first primer (33), producing for example truncated extension products (20). However, the target nucleic acid with the methylated cytosine is able to undergo primer extension with a first primer (32), thus forming a target nucleic acid extension product (dashed, (21)). The target nucleic acid and control nucleic can then be degraded (note the absence of (16) and (17), leaving behind any extension products. Amplifying the extension products can then be performed, here shown as a PCR using a first target specific primer (22) and a second target specific primer (23) for the target nucleic acid, and a first control specific primer (24) and a second control specific primer (25) for the control nucleic acid. Determining the difference between the amount of the target nucleic acid with the amount of a control nucleic acid lacking a methylated cytosine allows for quantitating methylation in the target nucleic acid. Here, amplification can proceed on the target extension product, but fails on the truncated control extension product.

Figure 5A:
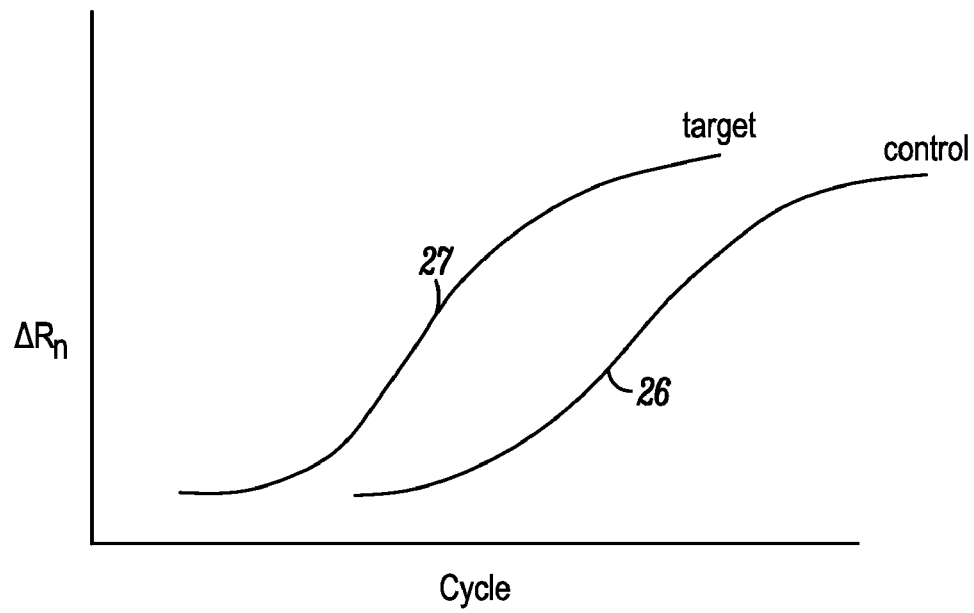
FIGS. 5A and 5B show illustrative graphs arising from an exemplary method of an embodiment of the present invention.

Representative graphs arising from practicing the method of FIG. 4, are depicted in FIG. 5. FIG. 5A shows the results of an experiment in which the target nucleic acid is more methylated than the control nucleic acid. Here, the results of a real-time PCR illustrate that the Ct value for the control nucleic acid (26) is higher (right-shifted) than the Ct value for the target nucleic acid (27). This shift reflects the greater number of extension products resulting from the extension reaction of the methylated target nucleic acid as compared to the control nucleic acid. This can be interpreted to reflect that the non-MeDNA binding protein preferentially bound control nucleic acids containing unmethylated cytosine, thus preventing the formation of control nucleic acid extension products. Thus, the target nucleic acids contain a greater amount of methylated cytosine at the cytosine position of interest than do the control nucleic acids.

Figure 5B:
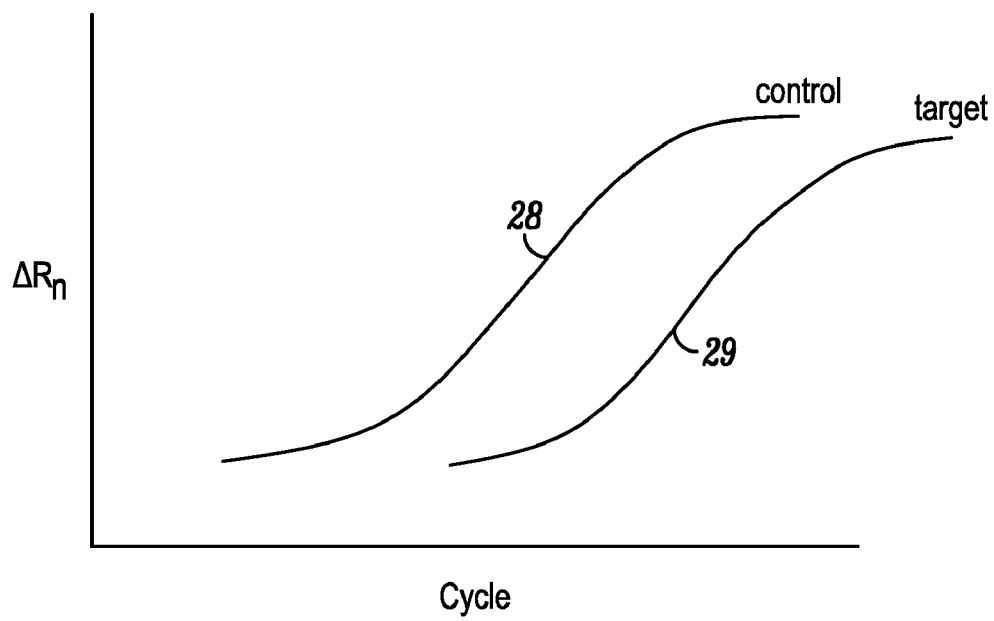

FIG. 5B shows the results of an experiment in which the target nucleic acid is less methylated than the control nucleic acid. Here, the results of a real-time PCR illustrate that the Ct value for the control nucleic acid (28) is lower (left-shifted) than the Ct value for the target nucleic acid (29). This shift reflects the greater number of extension products resulting from the extension reaction of the control nucleic acid as compared to the target nucleic acid. This can be interpreted to reflect that the non-MeDNA binding protein preferentially bound target nucleic acids containing unmethylated cytosine, thus preventing the formation of target nucleic acid extension products. Thus, the target nucleic acids contain a lesser amount of methylated cytosine at the cytosine position of interest than do the control nucleic acids.

Figure 6A:
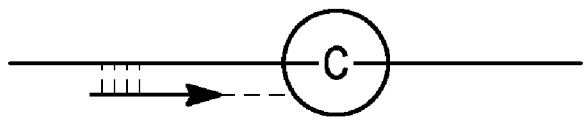
FIGS. 6A, 6B and 6C show schematic aspects of exemplary blocking complexes in accordance with embodiments of the present invention.
Figure 6B:
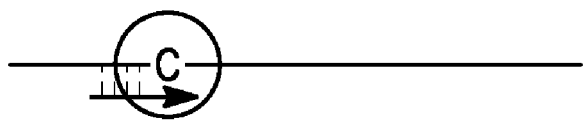
Figure 6C:
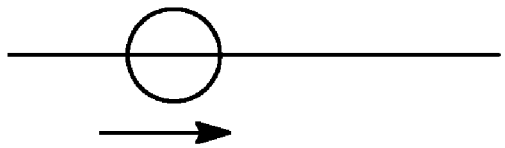
Figure 7B:
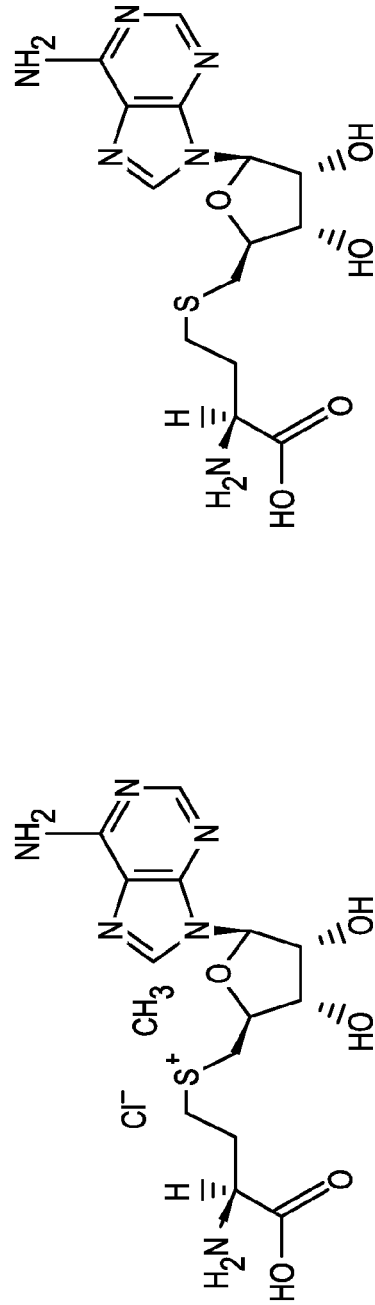
FIG. 7B shows exemplary nucleotides in accordance with embodiments of the present invention.
Figure 7B:
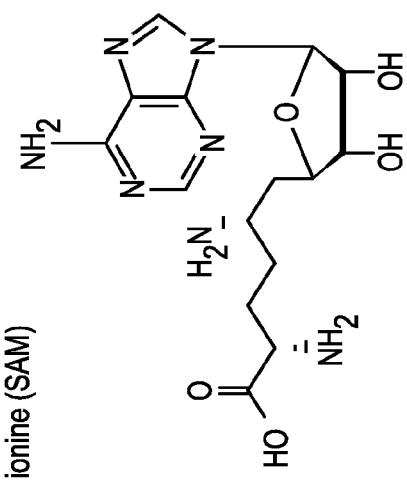
Figure 7C:
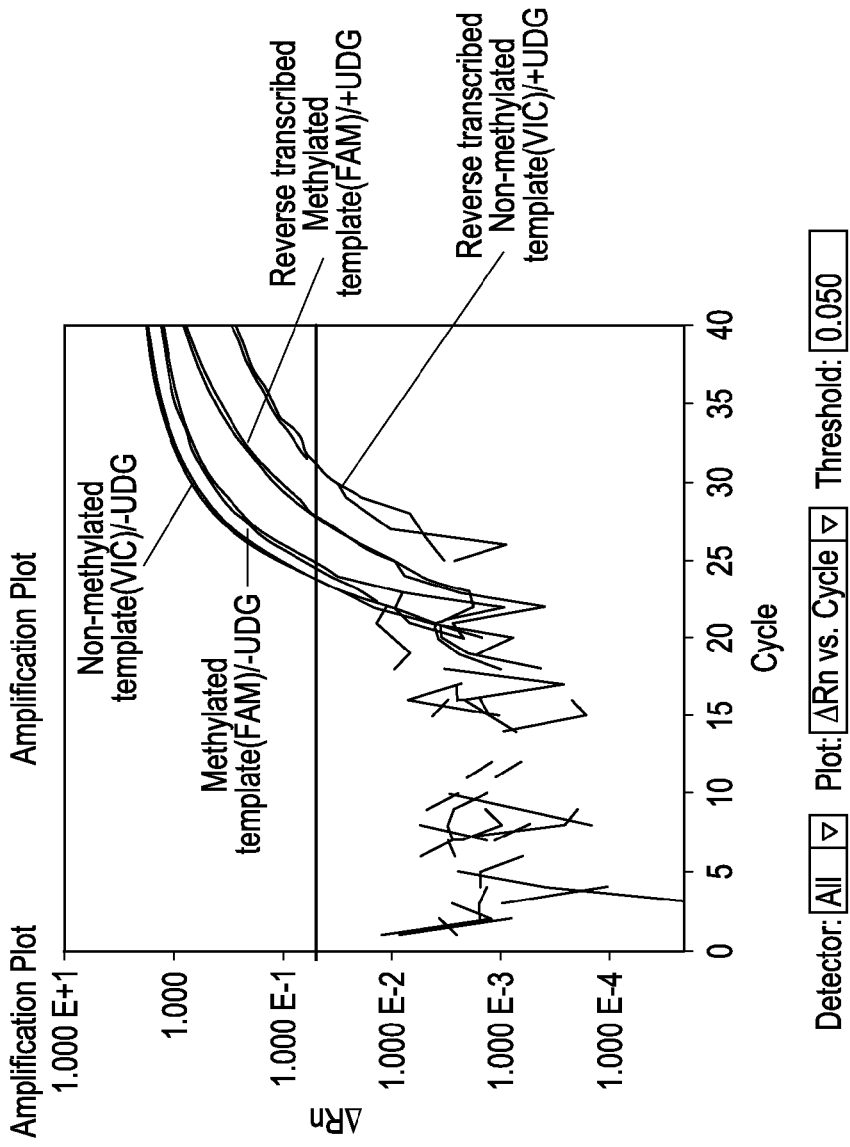
FIG. 7C shows an illustrative graph arising from an exemplary method of an embodiment of the present invention.
Figure 8:
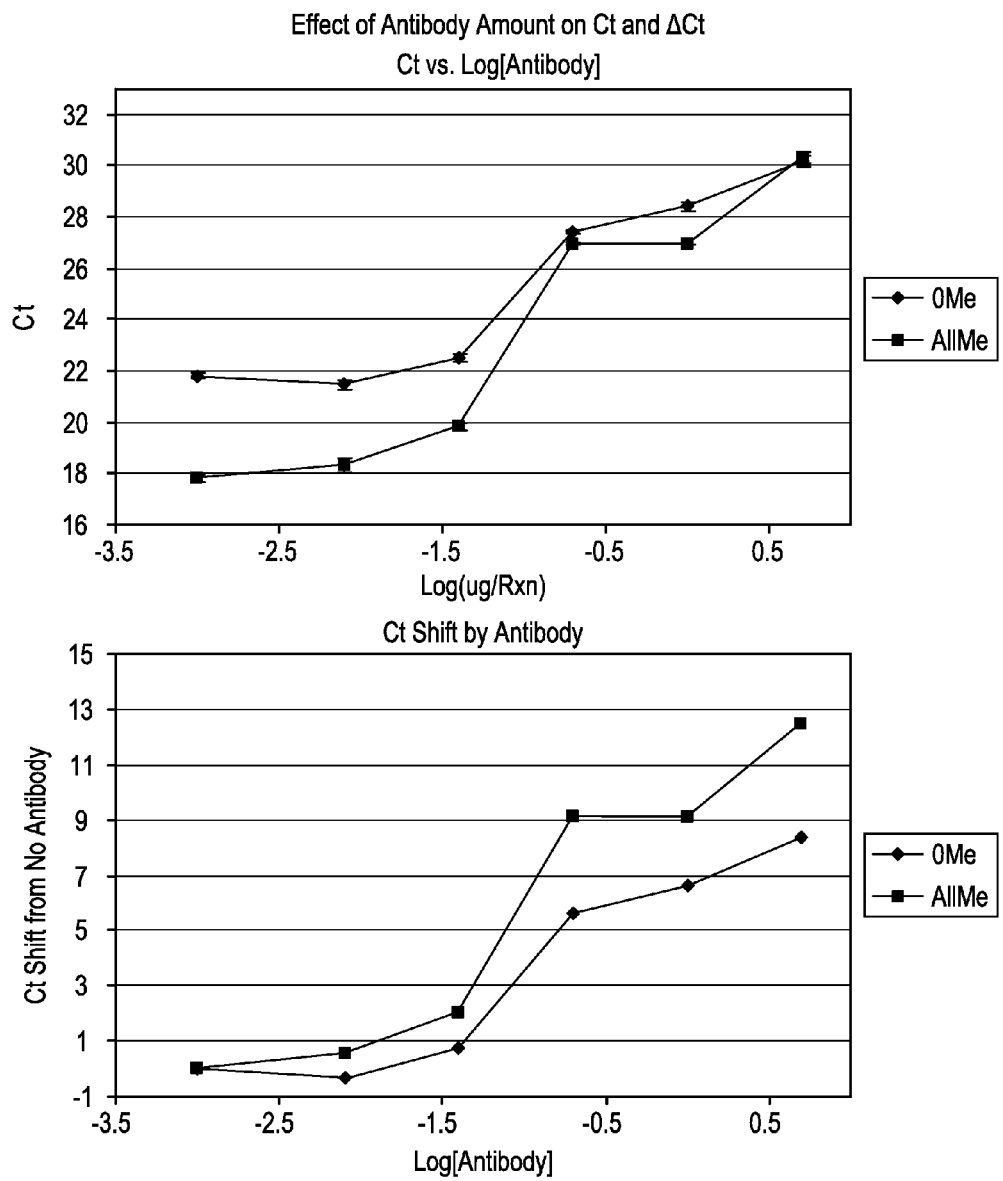
FIG. 8 shows illustrative graphs of an exemplary effect of antibody by amount on Ct and delta Ct in accordance with embodiments of the present invention.
Figure 9:
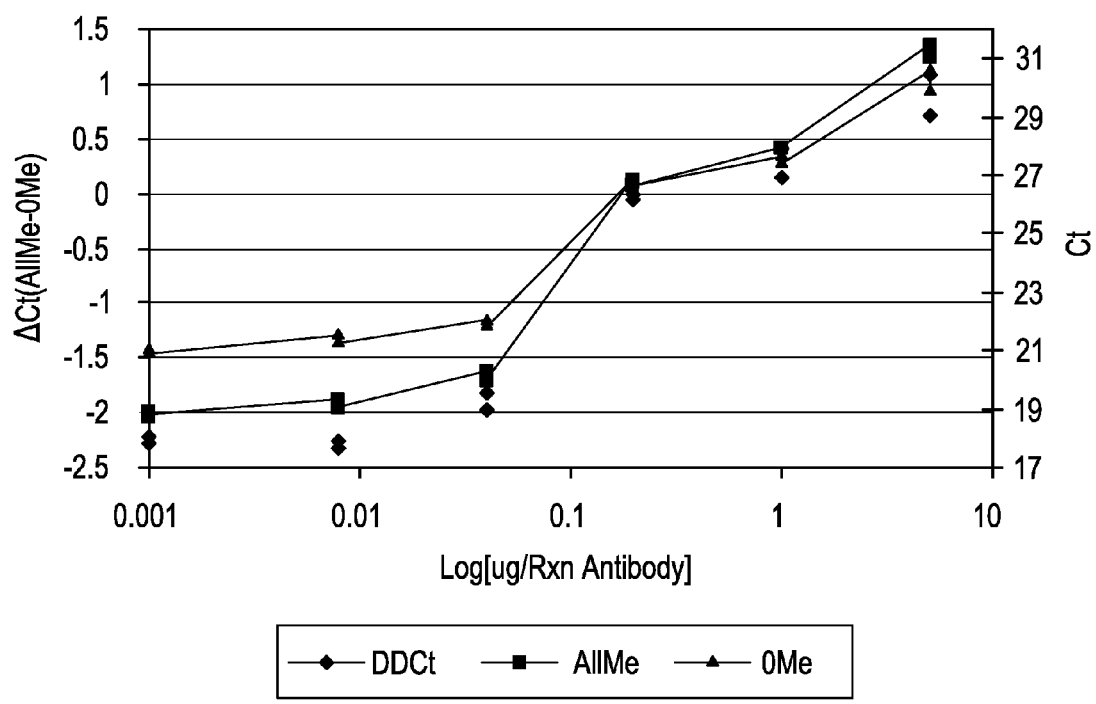
FIG. 9 shows an illustrative graph of an exemplary effect of antibody amount/duplex reaction in accordance with embodiments of the present invention.
Figure 10:
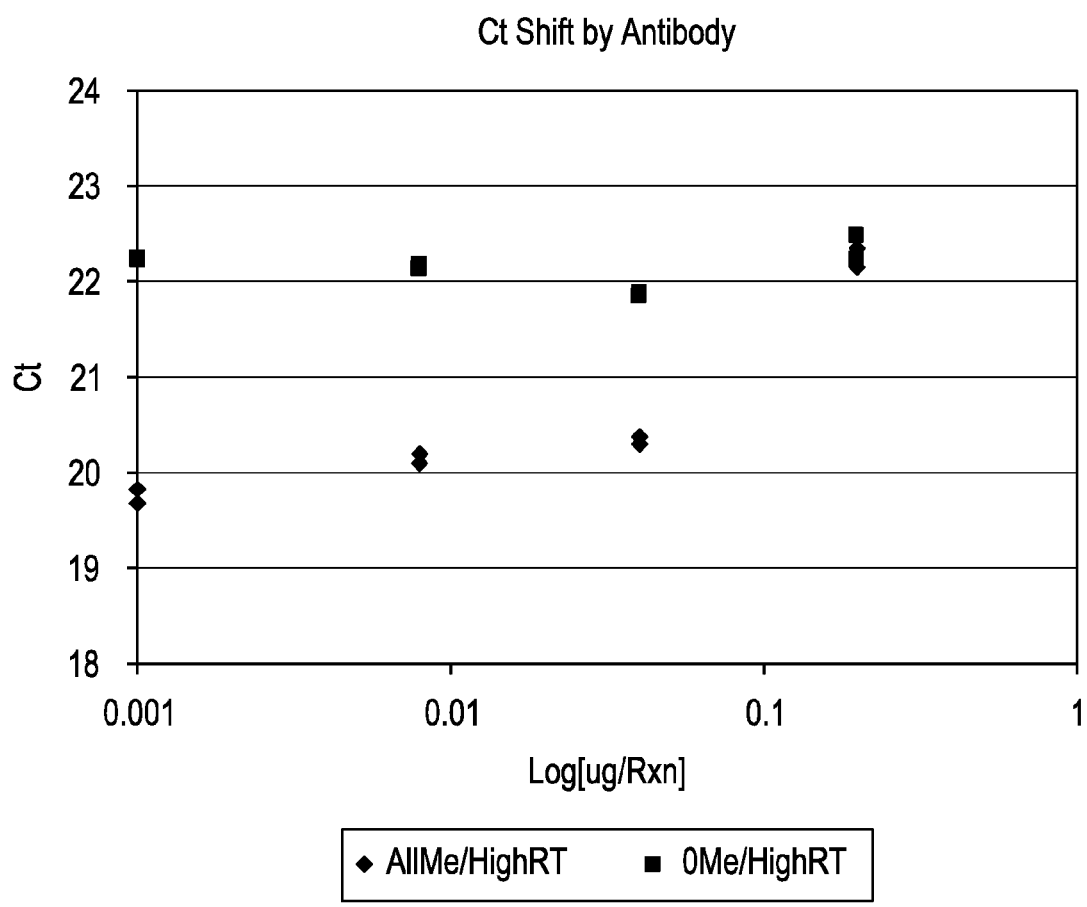
FIG. 10 shows an illustrative graph of an exemplary effect of antibody amount/duplex reaction: reduced Ct shift of OMe by increasing RT amount in accordance with embodiments of the present invention.
Figure 11:
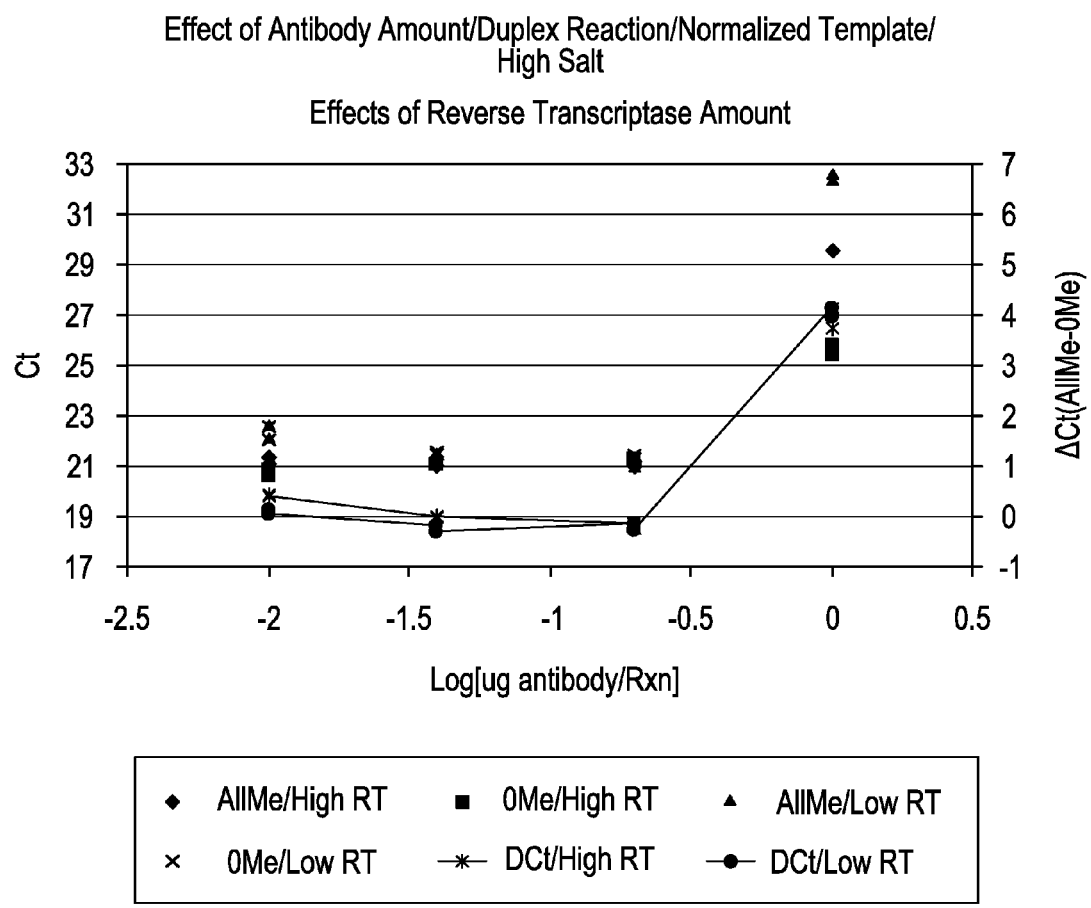
FIG. 11 shows an illustrative graph of an exemplary effect of antibody amount/duplex reaction with normalized template/high salt in accordance with embodiments of the present invention.

FIG. 6 illustrates the various possible relationships between the location of a cytosine of interest, the blocking complex formed with the MeDNA binding protein, and the first primer. In some embodiments, the first primer hybridizes upstream from the blocking complex formed by the non-MeDNA binding protein and the unmethylated cytosine in the target nucleic acid, and further extension of the first primer is blocked. This is depicted in FIG. 6A. Note that in FIG. 6A the first primer is shown hybridized (see vertical lines indicating Hydrogen bonds) upstream from the cytosine of interest, and that the primer is partially extended (dashed horizontal line). However, the blocking complex between the unmethylated cytosine and the non-MeDNA binding protein blocks further extension of the first primer. In some embodiments, the first primer hybridizes on the unmethylated cytosine on the blocking complex formed by the non-MeDNA binding protein and the unmethylated cytosine in the target nucleic acid, and initial extension of the first primer is blocked. This is depicted in FIG. 6B. Note than in FIG. 6B the first primer is shown hybridized (see the vertical lines indicating Hydrogen bonds) on the cytosine of interest, and that the primer is not extended. The blocking complex between the unmethylated cytosine and the non-MeDNA binding protein blocks initial extension of the first primer. In some embodiments, the first primer does not hybridize to the unmethylated cytosine on the blocking complex formed by the non-MeDNA binding protein and the unmethylated cytosine in the target nucleic acid. This is depicted in FIG. 6C. Note the absence of vertical lines between the first primer and the target nucleic acid, indicating that the blocking complex formed by the non-MeDNA binding protein and the unmethylated cytosine in the target nucleic acid prevents the first primer from hybridizing. As will be appreciated by one of ordinary skill in the art in light of the present teachings, the choice of position between the cytosine of interest, the non-MeDNA binding protein, and the primer binding site can be chosen according to the experimentalist using routine experimentation.

In view of FIG. 4, the control nucleic acid can be employed in a variety of ways. For example, the control nucleic acid can be in the same reaction mixture as the target nucleic acid and can be a different sequence than the target nucleic acid. The control nucleic acid can be of a known concentration, and can be known to contain an unmethylated cytosine at the position of interest. In some embodiments, the control nucleic acid can be in a different reaction mixture from the target nucleic acid. For example, the control nucleic acid can be the same sequence as the target nucleic acid, and can be present in a known amount in the different reaction mixture. In some embodiments, the control nucleic acid can be a different sequence than the target nucleic acid, and can be present in a known amount in the different reaction mixture. Various methods of performing the control reactions will be appreciated by one of skill in the art in light of the present teachings, including for example employing controls of the appropriate abundance class (see Bodeau et al., U.S. patent application Ser. No. 11/372,242).

The present teachings also provide a method of quantitating methylation in a target nucleic acid comprising;
  treating, in any order,
    (a) the control nucleic acid with a non-MeDNA binding protein, wherein the non-MeDNA binding protein forms a blocking complex with an unmethylated cytosine in the control nucleic acid lacking, wherein the unmethylated cytosine is disposed between a first control-specific primer binding site and a second control-specific primer binding site; and,
    (b) a target nucleic acid with a non-MeDNA binding protein, wherein the non-MeDNA binding protein fails to form a blocking complex with a methylated cytosine in the target nucleic acid, wherein the methylated cytosine is disposed between a first target specific primer binding site and a second target specific primer binding site;

extending, in any order,
(a) a first target specific primer hybridized to the first target specific primer binding site to form a target nucleic acid extension product; and,
(b) a first control specific primer hybridized to the first control specific primer binding site to form a control nucleic acid extension product;
degrading, in any order,
(a) the target nucleic acid; and,
(b) the control nucleic acid;
amplifying, in any order,
(a) the target nucleic acid extension product in a polymerase chain reaction comprising a first target specific primer and a second target specific primer; and,
(b) the control nucleic acid extension product in a polymerase chain reaction comprising a first control specific primer and a second control specific primer;
determining the difference between the amount of target nucleic acid with the amount of control nucleic acid; and,
quantitating methylation in the target nucleic acid.

In some embodiments, the determining comprises;
measuring, in any order,
(a) a first Ct value associated with the amount of the target nucleic acid, and,
(b) a second Ct value associated with the amount of the control nucleic acid; and,
quantitating methylation in the target nucleic by comparing the first Ct value with the second Ct value.

In some embodiments, the first Ct value is higher than the second Ct value, and the target nucleic acid is less methylated than the control nucleic acid.

In some embodiments, the first Ct value is lower than the second Ct value, and the target nucleic acid is more methylated than the control nucleic acid.

In some embodiments, the target nucleic acid and the control nucleic acid comprise the same first primer binding site and the same second primer binding site.

In some embodiments, the target nucleic acid is amplified in a separate reaction vessel from the control nucleic acid.

In some embodiments, the target nucleic acid and the control nucleic acid comprise the same first primer binding site and the same second primer binding site and are amplified with a common first primer and a common second primer.

In some embodiments, the target nucleic acid is amplified in a same reaction vessel as the control nucleic acid.

In some embodiments, the target nucleic acid and the control nucleic acid comprise a different first primer binding site and a different second primer binding site and are amplified with a different first primer and a different second primer.

In some embodiments, the quantitating comprises measuring an interchelating dye.

In some embodiments, the determining comprises;
measuring displacement of a target sequence specific probe, wherein the target sequence specific probe hybridizes to a region of the target nucleic acid extension product, or complement to the target nucleic acid extension product, disposed between the first target specific primer binding site and the second target specific primer binding site;
measuring displacement of a control sequence specific probe, wherein the control sequence specific probe hybridizes to a region of the control nucleic acid extension product, or complement to the control nucleic acid extension product, disposed between the first control specific primer binding site and the second control specific primer binding site.

In some embodiments, the treating with the non-MeDNA binding protein further comprises a cofactor.

In some embodiments, the cofactor is selected from the group consisting of S-adenosylmethionine, S-adenosylhomocysteine and sinefungin. In a preferred embodiment, S-adenosylhomocyceteine is used.

In some embodiments, the first primer hybridizes upstream from the blocking complex formed by the non-MeDNA binding protein and the unmethylated cytosine in the control nucleic acid, and further extension of the first primer is blocked.

In some embodiments, the first primer hybridizes on the unmethylated cytosine on the blocking complex formed by the non-MeDNA binding protein and the unmethylated cytosine in the control nucleic acid, and initial extension of the first primer is blocked.

In some embodiments, the first primer does not hybridize to the unmethylated cytosine on the blocking complex formed by the non-MeDNA binding protein and the unmethylated cytosine in the target nucleic acid.

Kits

The instant teachings also provide kits designed to expedite performing certain of the disclosed methods. Kits may serve to expedite the performance of certain disclosed methods by assembling two or more components required for carrying out the methods. In certain embodiments, kits contain components in pre-measured unit amounts to minimize the need for measurements by end-users. In some embodiments, kits include instructions for performing one or more of the disclosed methods. Preferably, the kit components are optimized to operate in conjunction with one another.

MeDNA Binding Protein Kits

In some embodiments, the present teachings provide a kit for quantitating methylation in a target nucleic acid comprising;
a Me-DNA binding protein;
a first target specific primer;
a second target specific primer;
a first control specific primer;
a second control specific primer; and,
a polymerase.

In some embodiments of the kit,
the first control specific primer is a different sequence from the first target specific primer; and,
the second control specific primer is a different sequence from the second target specific primer.

In some embodiments of the kit,
the first control specific primer is a same sequence as the first target specific primer; and,
the second control specific primer is a same sequence as the second target specific primer.

In some embodiments, the kit further comprises a control sequence specific probe.

In some embodiments, the kit further comprises a target sequence specific probe, wherein the control sequence specific probe is a different sequence from the target sequence specific probe.

In some embodiments, the kit further comprises a target sequence specific probe, wherein the control sequence specific probe is a same sequence as the target sequence specific probe.

In some embodiments, the kit comprises a cofactor.

Non-MeDNA Binding Protein Kits

In some embodiments, the present teachings provide a kit for quantitating methylation in a target nucleic acid comprising;
a non-MeDNA binding protein;
a first target specific primer;
a second target specific primer;

a first control specific primer;
a second control specific primer; and,
a polymerase.

In some embodiments of the kit,
the first control specific primer is a different sequence from the first target specific primer; and,
the second control specific primer is a different sequence from the second target specific primer.

In some embodiments, the first control specific primer is a same sequence as the first target specific primer; and,
the second control specific primer is a same sequence as the second target specific primer.

In some embodiments, the kit comprises a control sequence specific probe.

In some embodiments, the kit comprises a target sequence specific probe, wherein the control sequence specific probe is a different sequence from the target sequence specific probe.

In some embodiments, the kit comprises a target sequence specific probe, wherein the control sequence specific probe is a same sequence as the target sequence specific probe.

In some embodiments, the kit comprises a cofactor.

Although the disclosed teachings have been described with reference to various applications, methods, and kits, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

What is claimed is:

1. A method of quantitating methylation in a target nucleic acid comprising:
   treating a target nucleic acid with a MeDNA binding protein, wherein the MeDNA binding protein forms a blocking complex with a methylated cytosine in the target nucleic acid, wherein the methylated cytosine in the target nucleic acid is near a first target specific primer binding site;
   extending a first target specific primer hybridized to the first target specific primer binding site to form a target nucleic acid extension product;
   degrading the target nucleic acid;
   amplifying the target nucleic acid extension product;
   determining the difference between the amount of the target nucleic acid with the amount of a control nucleic acid lacking a methylated cytosine; and
   quantitating methylation in the target nucleic acid.

2. The method according to claim 1, wherein the amplifying comprises a polymerase chain reaction comprising a first target specific primer and a second target specific primer.

3. The method according to claim 1, wherein the degrading comprises treating the target nucleic acid with a nuclease, wherein the target nucleic acid extension product is resistant to the nuclease due to a blocking moiety in the first target specific primer.

4. A method of quantitating methylation in a target nucleic acid comprising:
   treating, in any order,
   (a) the target nucleic acid with a MeDNA binding protein, wherein the MeDNA binding protein forms a blocking complex with a methylated cytosine in the target nucleic acid, wherein the methylated cytosine is disposed between a first target specific primer binding site and a second target specific primer binding site; and,
   (b) a control nucleic acid with a MeDNA binding protein, wherein the MeDNA binding protein fails to form a blocking complex with an unmethylated cytosine in the control nucleic acid, wherein the non-methylated cytosine is disposed between a first control specific primer binding site and a second control specific primer binding site;
   extending, in any order,
   (a) a first target specific primer hybridized to the first target specific primer binding site to form a target nucleic acid extension product; and,
   (b) a first control specific primer hybridized to the first control specific primer binding site to form a control nucleic acid extension product;
   degrading, in any order,
   (a) the target nucleic acid; and,
   (b) the control nucleic acid;
   amplifying, in any order,
   (a) the target nucleic acid extension product in a polymerase chain reaction comprising a first target specific primer and a second target specific primer; and,
   (b) the control nucleic acid extension product in a polymerase chain reaction comprising a first control specific primer and a second control specific primer;
   determining the difference between the amount of target nucleic acid with the amount of control nucleic acid; and, quantitating methylation in the target nucleic acid.

5. The method of claim 4, wherein the determining comprises:
   measuring, in any order,
   (a) a first Ct value associated with the amount of the target nucleic acid, and,
   (b) a second Ct value associated with the amount of the control nucleic acid; and
   quantitating methylation in the target nucleic by comparing the first Ct value with the second Ct value.

6. The method of claim 4, wherein the first Ct value is higher than the second Ct value, and the target nucleic acid is more methylated than the control nucleic acid.

7. The method of claim 4, wherein the first Ct value is lower than the second Ct value, and the target nucleic acid is less methylated than the control nucleic acid.

8. The method of claim 4, wherein the target nucleic acid and the control nucleic acid comprise the same first primer binding site and the same second primer binding site.

9. The method according to claim 4, wherein the target nucleic acid is amplified in a separate reaction vessel from the control nucleic acid.

10. The method of claim 9, wherein the target nucleic acid and the control nucleic acid comprise the same first primer binding site and the same second primer binding site and are amplified with a common first primer and a common second primer.

11. The method according to claim 4, wherein the target nucleic acid is amplified in a same reaction vessel as the control nucleic acid.

12. The method of claim 11, wherein the target nucleic acid and the control nucleic acid comprise a different first primer binding site and a different second primer binding site and are amplified with a different first primer and a different second primer.

13. The method according to claim 4, wherein the quantitating comprises measuring an interchelating dye.

14. The method according to claim 4, wherein the determining comprises:
   measuring displacement of a target sequence specific probe, wherein the target sequence specific probe hybridizes to a region of the target nucleic acid extension product, or complement to the target nucleic acid extension product, disposed between the first target specific primer binding site and the second target specific primer binding site;
   measuring displacement of a control sequence specific probe, wherein the control sequence specific probe hybridizes to a region of the control nucleic acid extension product, or complement to the control nucleic acid extension product, disposed between the first control specific primer binding site and the second control specific primer binding site.

15. The method according to claim 4, wherein the treating with the MeDNA binding protein further comprises a cofactor.

16. The method according to claim 15 wherein the cofactor is selected from the group consisting of S-adenosylmethionine, S-adenosylhomocysteine and sinefungin.

17. The method according to claim 4, wherein the first primer hybridizes upstream from the blocking complex formed by the MeDNA binding protein and the methylated cytosine in the target nucleic acid, and further extension of the first primer is blocked.

18. The method according to claim 4, wherein the first primer hybridizes on the methylated cytosine on the blocking complex formed by the MeDNA binding protein and the methylated cytosine in the target nucleic acid, and initial extension of the first primer is blocked.

19. The method according to claim 4, wherein the first primer does not hybridize to the methylated cytosine on the blocking complex formed by the MeDNA binding protein and the methylated cytosine in the target nucleic acid.

20. A method of quantitating methylation in a target nucleic acid comprising:
   treating a control nucleic acid with a non-MeDNA binding protein, wherein the non-MeDNA binding protein forms a blocking complex with an unmethylated cytosine in the control nucleic acid, wherein the unmethylated cytosine in the control nucleic acid is near a first control specific primer binding site;
   extending a first primer hybridized to the first primer binding site to form a control nucleic acid extension product;
   degrading the control nucleic acid;
   amplifying the control nucleic acid extension product in a polymerase chain reaction comprising a first control specific primer and a second control specific primer;
   determining the difference between the amount of the control nucleic acid with the amount of a target nucleic acid containing a methylated cytosine; and
   quantitating methylation in the target nucleic acid.

21. The method according to claim 20, wherein the amplifying comprises a polymerase chain reaction comprising a first target specific primer and a second target specific primer.

22. The method according to claim 20, wherein the degrading comprises treating the target nucleic acid with a nuclease, wherein the target nucleic acid extension product is resistant to the nuclease due to a blocking moiety in the first target specific primer.

23. A method of quantitating methylation in a target nucleic acid comprising:
  treating, in any order,
    (a) the control nucleic acid with a non-MeDNA binding protein, wherein the non-MeDNA binding protein forms a blocking complex with an unmethylated cytosine in the control nucleic acid lacking, wherein the unmethylated cytosine is disposed between a first control-specific primer binding site and a second control specific primer binding site; and,
    (b) a target nucleic acid with a non-MeDNA binding protein, wherein the non-MeDNA binding protein fails to form a blocking complex with a methylated cytosine in the target nucleic acid, wherein the methylated cytosine is disposed between a first target specific primer binding site and a second target specific primer binding site;
  extending, in any order,
    (a) a first target specific primer hybridized to the first target specific primer binding site to form a target nucleic acid extension product; and,
    (b) a first control specific primer hybridized to the first control specific primer binding site to form a control nucleic acid extension product;
  degrading, in any order,
    (a) the target nucleic acid; and,
    (b) the control nucleic acid;
  amplifying, in any order,
    (a) the target nucleic acid extension product in a polymerase chain reaction comprising a first target specific primer and a second target specific primer; and,
    (b) the control nucleic acid extension product in a polymerase chain reaction comprising a first control specific primer and a second control specific primer;
  determining the difference between the amount of target nucleic acid with the amount of control nucleic acid; and, quantitating methylation in the target nucleic acid.

24. The method of claim 23, wherein the determining comprises:
  measuring, in any order,
    (a) a first Ct value associated with the amount of the target nucleic acid, and
    (b) a second Ct value associated with the amount of the control nucleic acid; and
  quantitating methylation in the target nucleic by comparing the first Ct value with the second Ct value.

25. The method of claim 23, wherein the first Ct value is higher than the second Ct value, and the target nucleic acid is less methylated than the control nucleic acid.

26. The method of claim 23 wherein the first Ct value is lower than the second Ct value, and the target nucleic acid is more methylated than the control nucleic acid.

27. The method of claim 23, wherein the target nucleic acid and the control nucleic acid comprise the same first primer binding site and the same second primer binding site.

28. The method according to claim 23, wherein the target nucleic acid is amplified in a separate reaction vessel from the control nucleic acid.

29. The method of claim 28, wherein the target nucleic acid and the control nucleic acid comprise the same first primer binding site and the same second primer binding site and are amplified with a common first primer and a common second primer.

30. The method according to claim 23, wherein the target nucleic acid is amplified in a same reaction vessel as the control nucleic acid.

31. The method of claim 30, wherein the target nucleic acid and the control nucleic acid comprise a different first primer binding site and a different second primer binding site and are amplified with a different first primer and a different second primer.

32. The method according to claim 23, wherein the quantitating comprises measuring an interchelating dye.

33. The method according to claim 23 wherein the determining comprises:
  measuring displacement of a target sequence specific probe, wherein the target sequence specific probe hybridizes to a region of the target nucleic acid extension product, or complement to the target nucleic acid extension product, disposed between the first target specific primer binding site and the second target specific primer binding site;
  measuring displacement of a control sequence specific probe, wherein the control sequence specific probe hybridizes to a region of the control nucleic acid extension product, or complement to the control nucleic acid extension product, disposed between the first control specific primer binding site and the second control specific primer binding site.

34. The method according to claim 23, wherein the treating with the non-MeDNA binding protein further comprises a cofactor.

35. The method according to claim 34, wherein the cofactor is selected from the group consisting of S-adenosylmethionine, S-adenosylhomocysteine and sinefungin.

36. The method according to claim 23, wherein the first primer hybridizes upstream from the blocking complex formed by the non-MeDNA binding protein and the unmethylated cytosine in the control nucleic acid, and further extension of the first primer is blocked.

37. The method according to claim 23, wherein the first primer hybridizes on the unmethylated cytosine on the blocking complex formed by the non-MeDNA binding protein and the unmethylated cytosine in the control nucleic acid, and initial extension of the first primer is blocked.

38. The method according to claim 23, wherein the first primer does not hybridize to the unmethylated cytosine on the blocking complex formed by the non-MeDNA binding protein and the unmethylated cytosine in the target nucleic acid.

* * * * *

SEQUENCE LISTING

```
<160> NUMBER OF SEQ ID NOS: 9

<210> SEQ ID NO 1
<211> LENGTH: 62
<212> TYPE: DNA
<213> ORGANISM: Artificial Sequence
<220> FEATURE:
<223> OTHER INFORMATION: Synthetic Template

<400> SEQUENCE: 1
ccccgcgagc acagataaat ggcttagmcg tagtttagta gggatcgtgc cggcgccagg     60
aa                                                                   62

<210> SEQ ID NO 2
<211> LENGTH: 62
<212> TYPE: DNA
<213> ORGANISM: Artificial Sequence
<220> FEATURE:
<223> OTHER INFORMATION: Synthetic Template

<400> SEQUENCE: 2
ccccgcgagc acagataaau ggcttagmcg uagttuagta gggaucgtgc cggcgccagg     60
aa                                                                   62

<210> SEQ ID NO 3
<211> LENGTH: 64
<212> TYPE: DNA
<213> ORGANISM: Artificial Sequence
<220> FEATURE:
<223> OTHER INFORMATION: Synthetic Template

<400> SEQUENCE: 3
ccccgcgagc acagataaau ggcttagmcg uagttuagta gggaucgtgc mcggmcgcca     60
ggaa                                                                 64

<210> SEQ ID NO 4
<211> LENGTH: 62
<212> TYPE: DNA
<213> ORGANISM: Artificial Sequence
<220> FEATURE:
<223> OTHER INFORMATION: Synthetic Template

<400> SEQUENCE: 4
ccccgcgagc acagataaau agggtttamc gugatuagtg gcgaucgtgc cggcgccagg     60
aa                                                                   62
```

```
<210> SEQ ID NO 5
<211> LENGTH: 15
<212> TYPE: DNA
<213> ORGANISM: Artificial Sequence
<220> FEATURE:
<223> OTHER INFORMATION: Forward Primer

<400> SEQUENCE: 5
ccccgcgagc acaga                                                        15

<210> SEQ ID NO 6
<211> LENGTH: 14
<212> TYPE: DNA
<213> ORGANISM: Artificial Sequence
<220> FEATURE:
<223> OTHER INFORMATION: Reverse Primer

<400> SEQUENCE: 6
ttcctgccgc cggc                                                         14

<210> SEQ ID NO 7
<211> LENGTH: 16
<212> TYPE: DNA
<213> ORGANISM: Artificial Sequence
<220> FEATURE:
<223> OTHER INFORMATION: Reverse Primer

<400> SEQUENCE: 7
ttcctggmcg cmcggc                                                       16

<210> SEQ ID NO 8
<211> LENGTH: 22
<212> TYPE: DNA
<213> ORGANISM: Artificial Sequence
<220> FEATURE:
<223> OTHER INFORMATION: Probe

<400> SEQUENCE: 8
tggcttagcg tagtttagta gg                                                22

<210> SEQ ID NO 9
<211> LENGTH: 22
<212> TYPE: DNA
<213> ORGANISM: Artificial Sequence
<220> FEATURE:
<223> OTHER INFORMATION: Probe

<400> SEQUENCE: 9
tagggtttac gtgattagtg gc                                                22
```